Dec. 17, 1974 C. MEYER Plant Pat. 3,668
ROSE PLANT
Filed Sept. 28, 1973
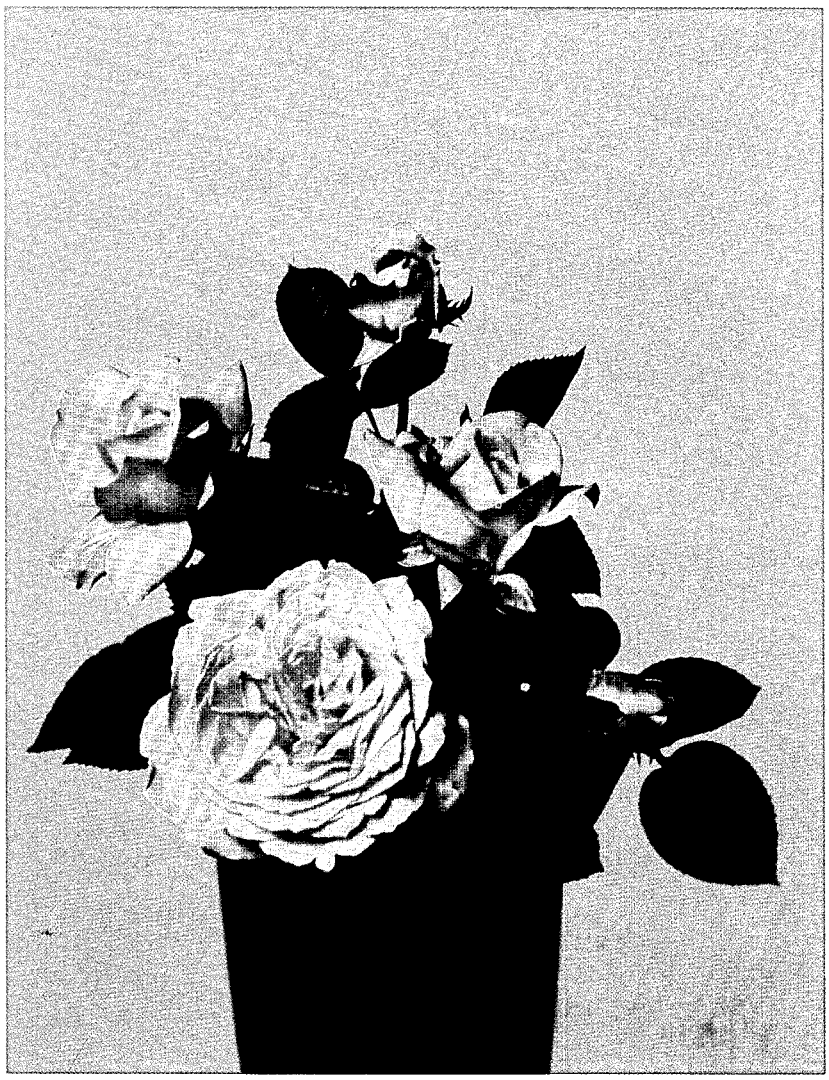

United States Patent Office

Plant Pat. 3,668
Patented Dec. 17, 1974

3,668
ROSE PLANT
Carl Meyer, Cleves, Ohio, assignor to
Geo. J. Ball Inc., West Chicago, Ill.
Filed Sept. 28, 1973, Ser. No. 401,881
Int. Cl. A01h 5/00
U.S. Cl. Plt.—20 1 Claim

ABSTRACT OF THE DISCLOSURE

A new variety of hybrid tea rose plant distinguished by its profuse and continuous producton of large, fluorescent, bright red blooms having a delicate fragrance and an exceptionally long lasting quality as cut flowers, the plant being much branched and vigorous in its growth habit and particularly suited as a garden rose.

BACKGROUND OF THE INVENTION

This new variety of rose plant originated as a seedling resulting from a cross of War Dance (P.P. 2,017) and Tropicana (P.P. 1,969) made by me during breeding efforts carried on in my gardens at Cleves, Ohio, since 1962 with the object of producing improved garden rose plants for the commercial market. This plant was discovered by me in 1965 and because it appeared to possess the most desirable characteristics of its parents, as well as a profuse production of large, well formed blossoms of unusual color, this plant was selected for propagation and testing. Asexual reproduction of this plant, by budding, carried on by me at Cleves, Ohio, since 1965 demonstrated that the desirable characteristics were well fixed and propagation through many successive generations, by budding, has shown the novel features to hold true from generation to generation. Commercial scale propagation of this new rose plant variety is now being carried on at McFarland, Calif.

DESCRIPTION OF THE DRAWING

My new variety of rose plant is illustrated by the accompanying full color photographic drawing which shows a full face view of the blossom and several stages of bud opening, the color shown being as nearly true as it is possible to obtain by means of conventional photographic procedures.

DESCRIPTION OF THE PLANT

The following is a detailed description of my new variety of garden rose plant with specifications of color according to Robert S. Wilson's Horticultural Colour Chart as issued by the British Colour Council and The Royal Horticultural Society.

THE PLANT

Origin: Seedling.
Parentage:
*Seed Parent.*—War Dance (P.P. 2,017).
*Pollen Parent.*—Tropicana (P.P. 1,969).
Classification:
*Botanic.*—*Rosa hybrida.*
*Commercial.*—Hybrid Tea.
Form: Bush.
Height: To at least four feet.
Growth: Vigorous and much branched.
Habit: Upright and sturdy, with good strength.

Foliage: Quantity—Abundant.
*Leaves.*—Shape—Odd pinnate. Size—5 x 3¾ inches.
*Leaflets.*—Three to seven in number. Shape—Ovate with serrated margins. Size—1½ to 1¾ inches wide x 1½ to 2 inches long. Texture—Smooth. Color—Upper Side—Spinach Green 960. Under Side—Spinach Green 960/1. Petioles—¼ inch long on side leaflets and ¾ inch long on top leaflet. Rachis—2 to 3 inches long, hairy and grooved. Thorns—Size ¼ to ⅜ inch long. Color—Reddish Green (in general).

THE BUD

Shape: Ovoid.
Size: Medium—About ¾ to 1 inch in diameter and about 1 inch in depth.
Color: Signal Red 719.
Opening rate: Slow.
Sepals: Spear shaped and hooded over bud. Sepals curl back upon opening of bud.
*Color.*—Inside—Light Green with White fuzz. Outside—Lettuce Green 861.
Calyx:
*Shape.*—Pear shaped.
*Size.*—Medium, ¾ inch wide x 1 inch long.
*Aspect.*—Hairy.
*Splitting.*—Calyx splits upon opening of bud.
Peduncle: 2 to 3 inches long. Slightly hairy and erect.
*Color.*—Lettuce Green 861.

THE FLOWER

Blooming Habit: Continuous and Profuse.
Size: Large. 4 inches in diameter and 2¼ inches in depth.
Borne: Singly.
Shape: High center when first opening flattening somewhat as bloom matures. Outer petals have undulating margins.
Petalage: Blossom has 35 to 40 petals in regular imbricated arrangement.
*Shape.*—Obovate with smooth edges.
*Color.*—Outer Petals—Signal Red 719/3 edged with Carmine Rose 621/1. Base—Near White. Inside Petals—Signal Red 719/3 edged with Carmine Rose 621/1. Reverse Side—Carmine 21/1.
Petaloids: 3 to 5 in number and of medium size.
*Color.*—Claret Rose 021/1.
Peduncle: Sturdy and upright, 2 to 3 inches long.
*Color.*—Lettuce Green 861.
Fragrance: Very slight.
Texture: Soft.
Appearance: Satiny.
Persistence: Petals stay on stem 10 to 15 days.
Discoloration: Color becomes slightly lighter as full bloom matures.
Effect of Weather: Bloom is slightly lighter in hot weather.
Lasting Quality: 10 to 15 days on the plant, 6 to 8 days as cut flower.

REPRODUCTIVE ORGANS

Stamens:
*Anthers.*—40 to 50 in number, ⅝ inch long and regularly arranged.
*Filaments.*—¼ inch long. Color—Generally, Pink.
*Pollen.*—Color—Yellow.
Pistils: 60 to 80 in number.
*Styles.*—¼ to about ⅜ inch long.
*Stigmas.*—Color—Generally, Light Yellow.

Characteristics of Ovaries: Color—Light Yellowish Green.
Fruit: None observed.

This new variety of garden rose plant is a vigorous grower, hardy and resistant to the usual rose diseases as observed at McFarland, Calif., where such diseases are ordinarily apt to be found. Its blossom color is outstanding and distinctly different than either of its parent varieties and, with the advantageous plant habit, this new plant is outstanding as a garden rose.

I claim:

1. A new and distinct garden variety of hybrid tea rose plant substantially as herein shown and described, characterized by the fluorescent red coloring of its large high centered blossoms which are produced continuously and profusely on vigorous, upright and much branched plants which reach a height of at least four feet.

No references cited.

ROBERT E. BAGWILL, Primary Examiner